(12) United States Patent
Izumi et al.

(10) Patent No.: US 8,123,987 B2
(45) Date of Patent: Feb. 28, 2012

(54) CHROMENE COMPOUNDS

(75) Inventors: Shinobu Izumi, Shunan (JP); Junji Takenaka, Shunan (JP)

(73) Assignee: Tokuyama Corporation, Shunan-Shi (JP)

( * ) Notice: Subject to any disclaimer, the term of this patent is extended or adjusted under 35 U.S.C. 154(b) by 245 days.

(21) Appl. No.: 12/223,115

(22) PCT Filed: Jan. 22, 2007

(86) PCT No.: PCT/JP2007/051318
§ 371 (c)(1),
(2), (4) Date: Jul. 23, 2008

(87) PCT Pub. No.: WO2007/086532
PCT Pub. Date: Aug. 2, 2007

(65) Prior Publication Data
US 2010/0230648 A1     Sep. 16, 2010

(30) Foreign Application Priority Data

Jan. 25, 2006  (JP) .................. 2006-016920
Jul. 3, 2006   (JP) .................. 2006-183502

(51) Int. Cl.
*G02B 5/23* (2006.01)
*C09B 56/12* (2006.01)

(52) U.S. Cl. ........ 252/586; 534/655; 546/196; 549/358; 549/381

(58) Field of Classification Search .......... 428/215, 428/137, 423.1, 412, 323, 411.1; 427/164, 427/162, 372.2, 299, 379, 384; 359/642; 264/1.32; 534/655; 549/381, 406, 200, 332, 549/330, 446, 510, 358, 382; 252/586; 568/325; 430/270.1; 528/420, 423.1; 257/E23.119; 504/105, 107; 544/586; 546/196
See application file for complete search history.

(56) References Cited

U.S. PATENT DOCUMENTS

| | | | |
|---|---|---|---|
| 5,783,116 A | 7/1998 | Lin | |
| 6,506,538 B1 | 1/2003 | Breyne et al. | |
| 6,558,583 B2 | 5/2003 | Breyne et al. | |
| 2004/0094753 A1* | 5/2004 | Izumi et al. | 252/586 |
| 2004/0242856 A1* | 12/2004 | Izumi et al. | 534/655 |

FOREIGN PATENT DOCUMENTS

| | | |
|---|---|---|
| EP | 1394156 A1 | 3/2004 |
| EP | 1433814 A1 | 6/2004 |
| EP | 1445257 A1 | 8/2004 |
| FR | 2815034 A1 | 4/2002 |
| JP | 2004-500319 A | 1/2004 |
| WO | WO-00/15628 A1 | 3/2000 |
| WO | WO 02/30916 A1 | 4/2002 |
| WO | WO-02/090342 A1 | 11/2002 |
| WO | WO-03/011967 A1 | 2/2003 |
| WO | WO-03/042203 A1 | 5/2003 |

OTHER PUBLICATIONS

Supplementary European Search Report datd Jan. 25, 2010 for European application No. 07707549.

* cited by examiner

*Primary Examiner* — Ling Choi
*Assistant Examiner* — Bijan Ahvazi
(74) *Attorney, Agent, or Firm* — Birch, Stewart, Kolasch & Birch, LLP

(57) ABSTRACT

Disclosed is a chromene compound represented by the following formula (1),

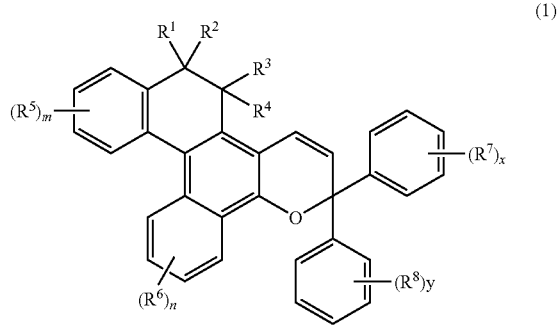

(1)

wherein $R^1$, $R^2$, $R^3$ and $R^4$ are, respectively, hydrogen atoms, alkyl groups, aryl groups, or the like groups under a condition that at least two of $R^1$ to $R^4$ are not hydrogen atoms, $R^5$, $R^6$, $R^7$ and $R^8$ are, respectively, alkyl groups, aryl groups or the like groups, m and n are, respectively, integers of 0 to 4, and x and y are, respectively, integers of 0 to 5.

4 Claims, No Drawings

CHROMENE COMPOUNDS

TECHNICAL FIELD

The present invention relates to novel chromene compounds and to the use of the chromene compounds.

BACKGROUND ART

Photochromism is a reversible action of a compound which quickly changes the color when it is irradiated with light containing ultraviolet rays, such as the sunlight or the light of a mercury lamp, and resumes its initial color when it is no longer irradiated with light and is placed in a dark place. The compound having the above properties is called photochromic compound and is used as a material of photochromic plastic lenses.

The photochromic compound used for the above application must satisfy such properties that:

(1) The compound has a low coloring degree (hereinafter referred to as initial color) in a region of visible light of before being irradiated with ultraviolet rays;

(2) The compound exhibits a high coloring degree (hereinafter called color density) when it is irradiated with ultraviolet rays;

(3) The compound enables the color density to increase to a saturation at a high rate, i.e., has a high color-developing sensitivity after it is irradiated with ultraviolet rays;

(4) The compound returns to the initial state at a high rate (hereinafter referred to as fading rate) after it is no longer irradiated with ultraviolet rays;

(5) The compound has a high recurring resistance in reversible action by light; and (6) The compound disperses well in a host material that is used or, concretely, the compound dissolves highly densely in a monomer composition that becomes the host material after cured.

Further, it has been desired that the photochromic plastic lenses develop a neutral tint such as brown or amber as a color tone in the state of developing color. Therefore, what color the photochromic compound will develop is a very important factor, as a matter of course.

When a desired color tone cannot be realized by the use of a single photochromic compound, the color tone is adjusted by mixing together a plurality of photochromic compounds that develop different color tones. In this case, it is important that the individual compounds that are mixed together have excellent properties and, besides, that the whole compounds (mixture) maintain balance in the properties.

From the standpoint of adjusting the color tone, it is important to use a photochromic compound which by itself develops a yellow color or a neutral tint. As the above compound, prior art 1 discloses a chromene compound [compound (A)] represented by the following formula (A), and the prior art 2 discloses a chromene compound [compound (B)] represented by the following formula (B). According to these prior arts, photochromic plastic lenses having favorable photochromic properties are obtained by using a curable composition which is obtained by dissolving the above photochromic compounds in a radically polymerizable monomer, and by molding (cast polymerizing) the curable composition by being cured by the thermoradical polymerization.

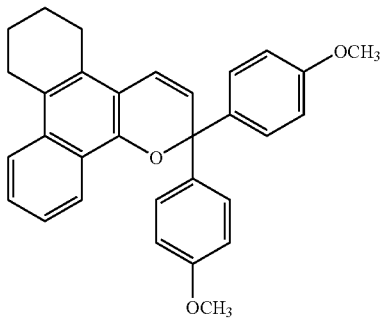

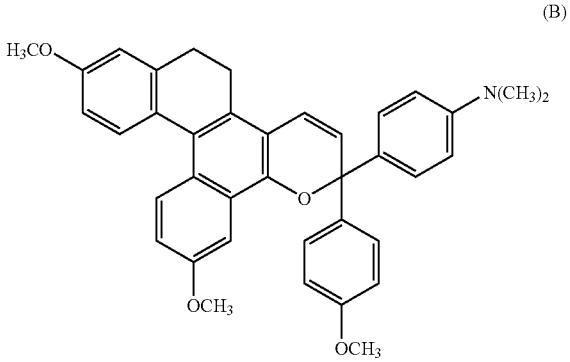

The method of producing the photochromic plastic lenses by the cast polymerization employed by the prior arts 1 and 2 (also called "in-mass" method or kneading method) is a representative method of producing photochromic plastic lenses imposing, however, a limitation on the kinds of the polymerizable monomers that can be used for obtaining favorable photochromic properties.

In recent years, attention has been given to a coating method as a method of producing photochromic plastic lenses without the above limitation (see prior art 3). According to the coating method, a coating agent comprising a polymerizable and curable composition containing a photochromic compound is applied onto the surface of the lens material, and the applied coating is cured to form a photochromic coating to thereby impart photochromic property to the lens material. Therefore, if a favorable coating adhesion is obtained, there is, in principle, no limitation on the lens material.

[Prior art 1] U.S. Pat. No. 5,783,116
[Prior art 2] Leaflet of International Laid-Open WO00/15628
[Prior art 3] Leaflet of International Laid-Open WO03/011967

DISCLOSURE OF THE INVENTION

According to the coating method, too, the developed color tone is adjusted in the same manner as the in-mass method, and it is important to use a photochromic compound which develops a yellow color or a neutral tint by itself. When the above compounds (A) and (B) are used for the coating method, however, it was clarified that a favorable photochromic coating layer cannot be obtained.

It is, therefore, an object of the present invention to provide a photochromic compound that can be used for the coating method without any problem and develops a yellow color or a neutral tint by itself.

According to the present invention, there is provided a chromene compound represented by the following formula (1),

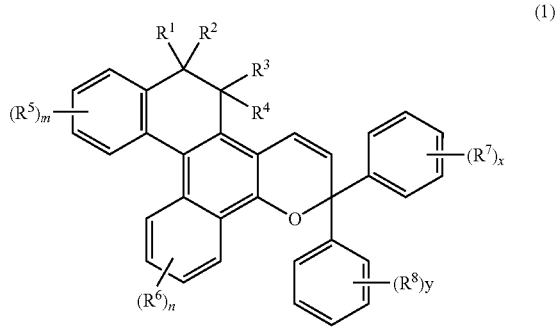

(1)

wherein $R^1$, $R^2$, $R^3$ and $R^4$ are, respectively, hydrogen atoms, hydroxyl groups, alkyl groups, cycloalkyl groups, alkoxy groups, aralkyl groups, aralkoxy groups or aryl groups under a condition that at least two of $R^1$ to $R^4$ are not hydrogen atoms, and $R^1$ and $R^2$ or $R^3$ and $R^4$ may be bonded together to form a ring, $R^5$, $R^6$, $R^7$ and $R^8$ are, respectively, hydroxyl groups, alkyl groups, cycloalkyl groups, alkoxy groups, aralkyl groups, aralkoxy groups, aryl groups, amino groups, substituted amino groups, cyano groups, nitro groups, halogen atoms, halogenalkyl groups or halogenoalkoxy groups, m and n are, respectively, integers of 0 to 4, and x and y are, respectively, integers of 0 to 5.

According to the present invention, there is further provided a photochromic curable composition containing a polymerizable monomer and the above chromene compound.

It is desired that the photochromic curable composition further contains a photopolymerization initiator.

According to the present invention, there is further provided a photochromic optical article having, as a constituent member, a high molecular formed body in which the chromene compound is dispersed.

According to the present invention, there is further provided an optical article comprising an optical material and a high molecular film formed on at least one surface of the optical material, the high molecular film having the above chromene compound dispersed therein. In this optical article, it is desired that the high molecular film is obtained by curing the photochromic curable composition containing a photopolymerization initiator by the photoradical polymerization.

Like the above compounds (A) and (B), the chromene compound of the present invention represented by the above formula (1) has a basic structure in which a 6-membered ring is condensed in a form of shearing a carbon atom at the fifth position and a carbon atom at the sixth position of the 2H-benzo[h]chromene skeleton. Unlike the above conventional compounds (A) and (B), however, the chromene compound of the present invention has a particular substituent bonded to the 6-membered ring, and exhibits excellent effects that will be described later owing to the presence of the above substituent. The above-mentioned prior arts 1 and 2 teach general formulas inclusive of the chromene compound of the present invention, but fail to disclose any concrete compounds that correspond to the chromene compound of the present invention to which the above particular substituent is bonded. Therefore, the chromene compound of the present invention is a novel compound.

When a photochromic coating layer containing a photochromic compound is formed on the surface of an optical material (e.g., lens) by the coating method, there is a limit on the amount of the photochromic compound that dissolves in the coating agent. To obtain a sufficient color density, therefore, the photochromic coating layer must be formed in a thickness of, for example, 30 to 50 μm. The coating agent is a liquid. In order to cure the layer of the coating agent applied onto the surface of a curved shape such as of a lens material maintaining the thickness without irregularity in the thickness, therefore, it is advantageous to utilize the photoradical polymerization which features a high curing rate.

Though clarified for the first time through the study by the present inventors, however, when it is attempted to polymerize and cure the photoradically polymerizable composition containing the above compound (A) or the above compound (B) by the irradiation with light, the compound easily reacts with the photoradical polymerization initiator to impair the polymerization and curing of the polymerizable monomer and, besides, undergoes the decomposition by itself to greatly decrease the photochromic property. This phenomenon presumably stems from a difference in the kind of the polymerization initiator though it does not occur at the time of the thermoradical polymerization.

On the other hand, the chromene compound of the present invention has a basic structure in common with the above-mentioned compounds (A) and (B), i.e., has a structure in which a 6-membered ring is condensed in a form of shearing a carbon atom at the fifth position and a carbon atom at the sixth position of the 2H-benzo[h]chromene skeleton with a particular substituent being bonded to the 6-membered ring. Therefore, the chromene compound of the invention exhibits strikingly improved stability while exhibiting excellent photochromic properties, very sparingly reacts with the optical and radical polymerization initiator even when it is irradiated with light in the presence of the optical and radical polymerization initiator, and makes it possible to form a coating having favorable photochromic properties. Further, even when cured by the thermoradical polymerization by being added to, for example, a polymerizable monomer, the chromene compound of the present invention exhibits superior recurring resistance in the photochromic properties to that of when the above compounds (A) and (B) are used.

The chromene compound of the present invention exhibits the above excellent effect because of the reason that the above basic structure (skeleton) helps exhibit the same effects as those of the compounds (A) and (B) concerning the developed color tone and photochromic properties and, besides, that since a particular substituent is bonded to the 6-membered ring of the basic structure, there is only one or zero methylene group (—$CH_2$—) that is subject to be attacked by a radical present on the 6-membered ring. As a result, the stability is markedly improved. That is, the compounds (A) and (B) have two methylene groups on the 6-membered ring and, therefore, have low stability, react with the photopolymerization initiator, and impair the photochromic properties.

BEST MODE FOR CARRYING OUT THE INVENTION

The chromene compound of the present invention is represented by the following formula (1),

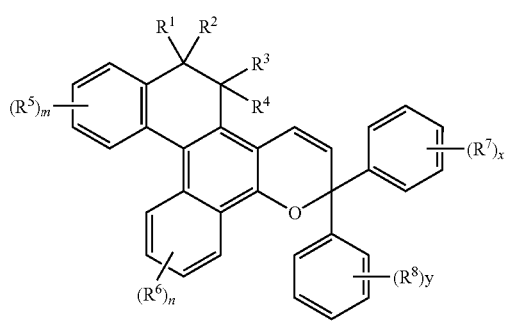

In the above formula (1), $R^1$, $R^2$, $R^3$ and $R^4$ are, respectively, (i) hydrogen atoms, (ii) hydroxyl groups, (iii) alkyl groups, (iv) cycloalkyl groups, (v) alkoxy groups, (vi) aralkyl groups, (vii) aralkoxy groups or (viii) aryl groups under a condition that at least two of $R^1$ to $R^4$ are not hydrogen atoms. Here, $R^1$ to $R^4$ may be the same or different from each other. Further, $R^1$ and $R^2$ may be bonded together to form (ix) a ring, or $R^3$ and $R^4$ may be bonded together to form (x) a ring.

If three or more of $R^1$ to $R^4$ are hydrogen atoms, the stability decreases and the effect of the invention is not obtained. From the standpoint of effect, it is desired that $R^1$ and $R^2$ are not hydrogen atoms simultaneously, and $R^3$ and $R^4$ are not hydrogen atoms simultaneously (i.e., no methylene group ($>CH_2$) is present on the 6-membered ring to which $R^1$ to $R^4$ are bonded) and it is further desired that at least three of $R^1$ to $R^4$ are not hydrogen atoms.

There is no particular limitation on $R^1$ to $R^4$ which are (iii) the alkyl groups. Generally, however, alkyl groups with 1 to 9 carbon atoms are preferred. Preferred examples of the alkyl group include methyl group, ethyl group, n-propyl group, isopropyl group, n-butyl group, sec-butyl group and tert-butyl group.

There is no particular limitation on (iv) the cycloalkyl groups. Generally, however, preferred examples are cyclopropyl group, cyclobutyl group, cyclopentyl group, cyclohexyl group, cycloheptyl group or cyclooctyl group having 3 to 12 carbon atoms.

There is no particular limitation on (v) the alkoxy groups. Generally, however, preferred examples are methoxy group, ethoxy group, n-propoxy group, isopropoxy group, n-butoxy group, sec-butoxy group or tert-butoxy group having 1 to 5 carbon atoms.

There is no particular limitation on (vi) the aralkyl groups. Generally, however, preferred examples are those having 7 to 11 carbon atoms, such as benzyl group, phenylethyl group, phenylpropyl group or phenylbutyl group.

There is no particular limitation on (vii) the aralkoxy group. Generally, however, preferred examples are those having 6 to 10 carbon atoms, such as phenoxy group or naphthoxy group.

There is no particular limitation on (viii) the aryl groups. Preferably, however, there can be exemplified an aromatic hydrocarbon group having 6 to 10 carbon atoms or an aromatic heterocyclic group having 4 to 12 carbon atoms that form a ring. Concretely, there can be exemplified phenyl group, naphthyl group, thienyl group, furyl group, pyrrolinyl group, pyridyl group, benzothienyl group, benzofuranyl group, or benzopyrrolinyl group. There can be, further, preferably used a substituted aryl group of which the one or more or more hydrogen atoms are substituted by alkyl groups, alkoxy groups, aralkyl groups or aralkoxy groups which are the same as those described above.

As the ring (ix) formed by $R^1$ and $R^2$ bonded together or as the ring (x) formed by $R^3$ and $R^4$ bonded together, there can be preferably used an aliphatic hydrocarbon ring having 4 to 10 carbon atoms that form the ring. Further, the ring may be condensed with an aromatic hydrocarbon ring such as benzene or naphthalene. The ring may have, as a substituent, an alkyl group or an alkoxy group having 1 to 5 carbon atoms. Particularly preferred examples of the ring are shown below in the form of cyclic groups (divalent cyclic groups with "6-membered carbon atoms" in which $R^1$ and $R^2$ are bonded together or with "6-membered carbon atoms" in which $R^3$ and $R^4$ are bonded together as spiro carbon atoms).

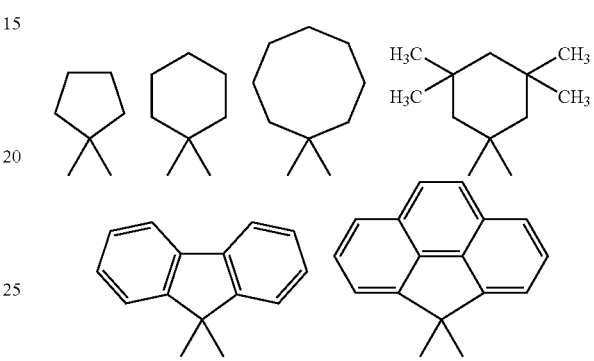

In the above formula (1), $R^5$, $R^6$, $R^7$ and $R^8$ which are the substituents bonded to the ring are, respectively, hydroxyl groups, alkyl groups, cycloalkyl groups, alkoxy groups, aralkyl groups, aralkoxy groups, aryl groups, amino groups, substituted amino groups, cyano groups, nitro groups, halogen atoms, halogenalkyl groups or halogenoalkoxy groups.

Here, the alkyl groups, cycloalkyl groups, alkoxy groups, aralkyl groups, aralkoxy groups and aryl groups are the same as those of $R^1$ to $R^4$ described above, and preferred groups are also the same as those exemplified above.

Though there is no particular limitation on the substituted amino group, preferred examples include those in which an alkyl group or an aryl group is bonded to a nitrogen atom, such as alkylamino group, dialkylamino group, arylamino group or diarylamino group. Concrete examples include methylamino group, ethylamino group, phenylamino group, dimethylamino group, diethylamino group and diphenylamino group.

As other preferred substituted amino group, there can be exemplified heterocyclic groups in which two substituents bonded to nitrogen atoms are bonded together to form a heterocyclic ring, such as morphorino group, piperidino group, pyrrolidinyl group, piperadino group, N-methylpiperadino group and indolinyl group.

As the halogen atom, there can be exemplified fluorine atom, chlorine atom, bromine atom or iodine atom.

As the halogenoalkyl group, there can be exemplified those in which one or two or more hydrogen atoms of the alkyl group are substituted by fluorine atoms, chlorine atoms or bromine atoms. Among them, the ones substituted with fluorine atoms are preferred. Preferred examples of the halogenoalkyl group include fluoromethyl group, difluoromethyl group and trifluoromethyl group.

As the halogenoalkoxy group, there can be exemplified those in which one or two or more hydrogen atoms of the alkoxy group are substituted by fluorine atoms, chlorine atoms or bromine atoms. Among them, the ones substituted with fluorine atoms are preferred. Particularly preferred examples of the halogenoalkoxy group include fluoromethoxy group, difluoromethoxy group and trifluoromethoxy group.

In the above formula (I), m, n, x and y denote the numbers of the substituents $R^5$, $R^6$, $R^7$ and $R^8$, wherein m and n are, respectively, integers of 0 to 4, preferably, integers of 0 to 2 and x and y are, respectively, integers of 0 to 5, preferably, integers of 0 to 2, and when two $R^6$ are bonding to adjacent carbon atoms, bonded two group $R^6$ may form 1,3-dioxolan ring or 1,4-dioxane ring and these rings may have an alkyl group as a substituent.

Described below are concrete examples of the chromene compound that can be particularly preferably used in the present invention.

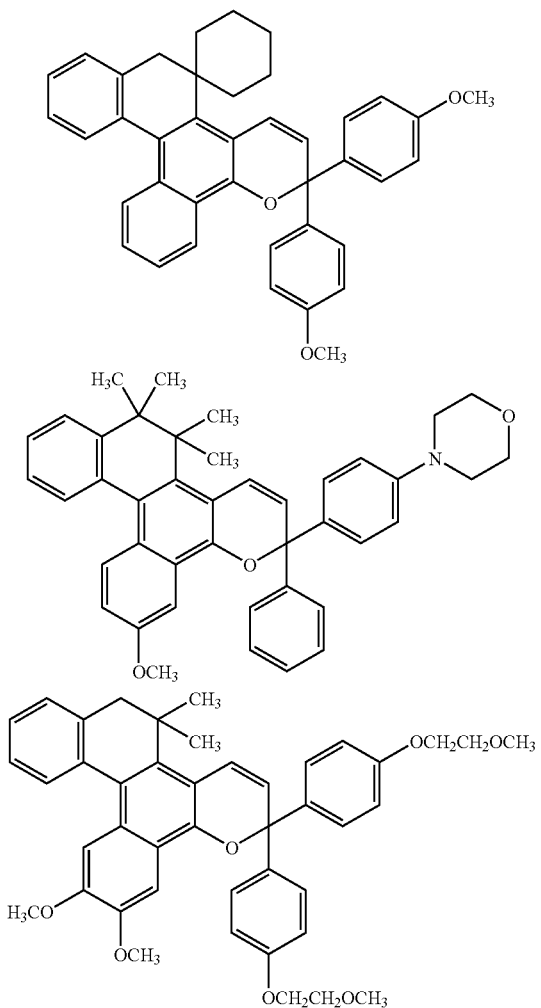

The chromene compounds of the present invention usually exist as solids or viscous liquids which are colorless or faintly yellow under normal temperature and normal pressure, and can be confirmed by the following means (I) to (III).

(I) Upon measuring the proton nuclear magnetic resonance spectra ($^1$H-NMR), there appear peaks near δ 5.0 to 9.0 ppm based on the aromatic proton and the proton of alkene and peaks near δ 1.0 to 4.0 ppm based on the proton of alkyl group and the proton of alkylene group. Further, the number of protons of the bonded groups can be learned by comparing their spectral intensities.

(II) The compositions of the corresponding products can be determined by the elemental analysis.

(III) Upon measuring the $^{13}$C-nuclear magnetic resonance spectra ($^{13}$C-NMR), there appear peaks based on the carbon atom of an aromatic hydrocarbon group near δ 110 to 160 ppm, peaks based on the carbon atoms of an alkene and an alkyne near δ 80 to 140 ppm, and peaks based on the carbon atoms of an alkyl group and an alkylene group near δ 20 to 80 ppm.

The chromene compounds of the present invention can be preferably produced by, for example, reacting a naphthol derivative represented by the following formula (2) with a propargyl alcohol derivative represented by the following formula (3) in the presence of an acid catalyst.

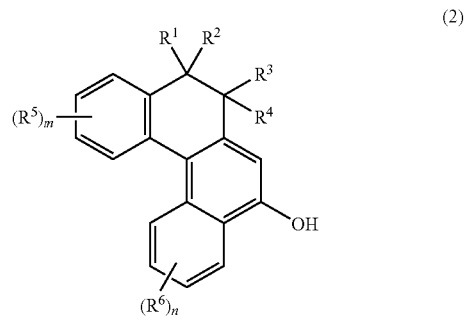

wherein $R^1$ to $R^6$, m and n are as defined in the above formula (1),

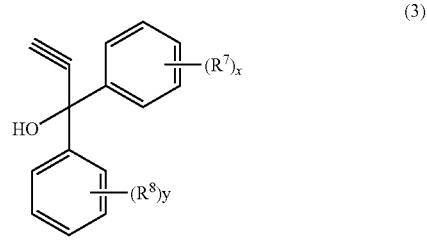

wherein $R^7$, $R^8$, x and y are as defined in the above formula (1).

The propargyl alcohol derivative represented by the above general formula (3) can be synthesized by reacting a ketone derivative of a corresponding structure with a metal acetylene compound such as lithium acetylide.

When the compound represented by the above formula (2) is reacted with the compound represented by the above formula (3), it is desired to use the compound of the formula (3) in an amount of 0.5 to 2 mols and, particularly, 0.8 to 1.5 mols per mol of the compound of the formula (2). As the acid catalyst, there can be used sulfuric acid, benzenesulfonic acid, p-toluenesulfonic acid or acid alumina. The amount of use of the acid catalyst may be in a range of 0.1 to 10 parts by mass per a total amount of 100 parts by mass of the compound of the formula (2) and the compound (reaction substrate) of the formula (3). The reaction is preferably conducted in the presence of a solvent. As the solvent, there is used a nonprotonic organic solvent, such as N-methylpyrrolidone, dimethylformamide, tetrahydrofuran, benzene or toluene. The reaction is usually conducted at 0 to 200° C. and, preferably, by refluxing the solvent.

After the reaction, a desired product is isolated from the obtained crude product through the silica gel column refining and further, as required, through the recrystallization.

The chromene compound of the present invention dissolves well in a general organic solvent such as toluene, chloroform or tetrahydrofuran. When the chromene compound of the present invention is dissolved in the above solvent, the solution thereof is, usually, in nearly a colorless and clear state. The solution exhibits a favorable photochromic phenomenon quickly developing a color when it is irradiated with sunlight or ultraviolet rays and quickly and reversibly assuming its initial colorless state when light is shut off.

Further, the chromene compound of the present invention exhibits similar photochromic properties even in a high molecular solid matrix (high molecular formed body). The high molecular solid matrix may be any one provided it permits the chromene compound of the present invention to be homogeneously dispersed therein. Preferably, there can be exemplified a thermoplastic resin and a cured body of a radically polymerizable and curable composition containing a radically polymerizable polyfunctional monomer.

Optically preferred examples of the thermoplastic resin include polymethylacrylate, polyethylacrylate, polymethylmethacrylate, polyethylmethacrylate, polystyrene, polyacrylonitrile, polyvinyl alcohol, polyacrylamide, poly(2-hydroxyethyl methacrylate), polydimethylsiloxane, and polycarbonate.

As the radically polymerizable polyfunctional monomer contained in the above radically polymerizable and curable composition, there can be exemplified the following compounds (a) to (e).

(a) Polyvalent acrylic and polyvalent methacrylic ester compounds such as ethylene glycol diacrylate, diethylene glycol dimethacrylate, triethylene glycol dimethacrylate, tetraethylene glycol dimethacrylate, ethylene glycol bisglycidyl methacrylate, bisphenol A dimethacrylate, 2,2-bis(4-methacryloyloxyethoxyphenyl)propane, and 2,2-bis(3,5-dibromo-4-methacryloyloxyethoxyphenyl)propane;

(b) Polyvalent allyl compounds such as diallyl phthalate, diallyl terephthalate, diallyl isophthalate, diallyl tartarate, diallyl epoxysuccinate, diallyl fumarate, diallyl chloroendoate, diallyl hexaphthalate, diallyl carbonate, allyl diglycol carbonate and trimethylolpropanetriallyl carbonate;

(c) Polyvalent thioacrylic and polyvalent thiomethacrylic ester compounds such as 1,2-bis(methacryloylthio)ethane, bis(2-acryloylthioethyl)ether, and 1,4-bis(methacryloylthiomethyl)benzene;

(d) Acrylic ester compounds and methacrylic ester compounds such as glycidyl acrylate, glycidyl methacrylate, β-methylglycidyl methacrylate, bisphenol A-monoglycidyl ether methacrylate, 4-glycidyloxy methacrylate, 3-(glycidyl-2-oxyethoxy)-2-hydroxypropyl methacrylate, 3-(glycidyloxy-1-isopropyloxy)-2-hydroxypropyl acrylate, 3-glycidyloxy-2-hydroxypropyloxy)-2-hydroxypropyl acrylate; and (e) Divinylbenzene.

As other monomers that can be contained in the above radically polymerizable and curable composition, there can be exemplified the following compounds (f) to (j).

(f) Unsaturated carboxylic acids such as acrylic acid, methacrylic acid and anhydrous maleic acid;

(g) Acrylic and methacrylic ester compounds such as methyl acrylate, methyl methacrylate, benzyl methacrylate, phenyl methacrylate, and 2-hydroxyethyl methacrylate;

(h) Fumaric ester compounds such as diethyl fumarate and diphenyl fumarate;

(i) Thioacrylic and thiomethacrylic ester compounds such as methylthioacrylate, benzylthioacrylate and benzylthiomethacrylate; and (i) Vinyl compounds such as styrene, chlorostyrene, methylstyrene, vinylnaphthalene, α-methylstyrene dimer and bromostyrene.

The chromene compound of the present invention develops a yellow color or a neutral tint by itself, exhibits not only favorable photochromic properties but also very high stability, and reacts sparingly with the photoradical polymerization initiator even when it is irradiated with light in the presence of the photoradical polymerization initiator. Even when dispersed in the curable composition that will be cured by photoradical polymerization, therefore, the chromene compound of the present invention does not impair the curing and makes it possible to obtain a cured body exhibiting favorable photochromic properties. Therefore, the chromene compound of the present invention is very useful as a component for the photochromic coating agent that is used at the time of producing a photochromic plastic lens by the coating method. Owing to its high degree of stability, further, excellent recurring resistance is obtained in the photochromic properties when the chromene compound of the present invention is polymerized and cured being dispersed in the curable composition of the type that is cured by the thermoradical polymerization. Therefore, the chromene compound of the present invention is highly useful as a material for producing photochromic plastic lenses by the in-mass method.

When the chromene compound of the invention is used as a photoradically polymerizable composition that is used as a photochromic coating agent at the time of producing the photochromic plastic lenses by the coating method or is used as a thermopolymerizable composition that is a starting material at the time of producing the photochromic plastic lenses by the in-mass method, the polymerizable compositions are prepared and used in the same manner as those of the prior art but using the chromene compound of the invention as a photochromic compound component.

When, for example, a photoradically curable composition is to be obtained, the chromene compound of the present invention may be added in an amount of 0.01 to 20 parts by mass and, preferably, 0.1 to 10 parts by mass, and the photoradical polymerization initiator may be added in an amount of 0.001 to 10 parts by mass and, preferably, 0.01 to 5 parts by mass per 100 parts by mass of the radically polymerizable and curable composition that contains the above radically polymerizable polyfunctional monomer. In order to adjust the color tone that develops, the above composition may be blended with photochromic compounds other than the chromene compound of the present invention, as a matter of course.

Described below are preferred examples of the photoradical polymerization initiator that can be used.

Benzoin;
Benzoinmethyl ether,
Benzoinbutyl ether;
Benzopenol;
Acetophenone 4,4'-dichlorobenzophenone;
Diethoxyacetophenone;
2-Hydroxy-2-methyl-1-phenylpropane-1-one;
Benzylmethylketal;
1-(4-Isopropylphenyl)-2-hydroxy-2-methylpropane-1-one;
1-Hydroxycyclohexylphenylketone;
2-Isopropylthiooxanthone;
Bis(2,6-dimethoxybenzoyl-2,4,4-trimethyl-pentylphosphinoxide;
Bis(2,4,6-trimethylbenzoyl)-phenylphosphinoxide;

2,4,6-Trimethylbenzoyldiphenyl-phosphinoxide; and
2-Benzyl-2-dimethylamino-1-(4-morpholinophenyl)-butanone-1.

A preferred composition of when the photocurable composition is used as a photochromic coating agent has been described, for example, in a leaflet of International Laid-Open No. 03/011967. When the chromene compound of the invention is to be used, too, therefore, the composition may be optimized in accordance with the description of the above patent document.

The thus prepared photochromic coating agent can be used in a customary manner. For example, the optical base member such as a lens material is suitably pretreated and is spin-coated with a coating solution containing the chromene compound of the present invention and is cured by the irradiation with light in a nitrogen atmosphere to form a high molecular film (photochromic layer) in which the chromene compound is dispersed on at least one surface of the optical material. As the pretreatment for the optical material, there has been known washing the surfaces with an organic solvent or with an alkaline aqueous solution, corona treatment and primer treatment, which may be suitably selected depending upon the kind of the material. On the photochromic coating that is formed, a hard coating or a reflection-preventing coating is further formed, as required.

By using the chromene compound of the present invention, a photochromic plastic lens can be produced by a method other than the in-mass method or the coating method. For example, the following methods can be employed.
(a) The thermoplastic resin and the chromene compound of the present invention are kneaded together in a molten state, dispersed in a resin, and are molded.
(b) A polymer film in which the photochromic material of the present invention is homogeneously dispersed is sandwiched in a lens.
(c) A solution is prepared by dissolving the chromene compound of the present invention in, for example, a silicone oil, the obtained solution and a plastic lens are contacted with each other at 150 to 200° C. so that the chromene compound of the present invention disperses and permeates into the plastic lens matrix, and the surfaces thereof are coated with a curable material (imbibition method).

Further, the chromene compound of the present invention can be used in a wide range of applications in addition to the photochromic plastic lenses. For example, the chromene compound can be used as various memory materials to substitute for a silver salt photosensitive material, as a copying material, as a photosensitive material for printing, as a memory material for CRTs, as a photosensitive material for laser and as a photosensitive material for holography. Further, the photochromic material using the chromene compound of the present invention can be utilized as a photochromic lens material, as an optical filter material, as a display material, as an actinometer and as an ornamental material.

The chromene compound of the present invention has a feature of developing a yellow color or a neutral tint by itself. When used for the photochromic lenses, the chromene compound of the present invention may be used by itself or may be used in combination with any other plurality of photochromic compounds to obtain a desired color tone. As the photochromic compounds that can be used in combination with the chromene compound of the present invention, there can be used known photochromic compounds such as naphthopyran compound, chromene compounds other than the chromene compound of the present invention, spirooxazine compound, spiropyran compound and fulgimide compound. Concretely, the following photochromic compounds can be used.

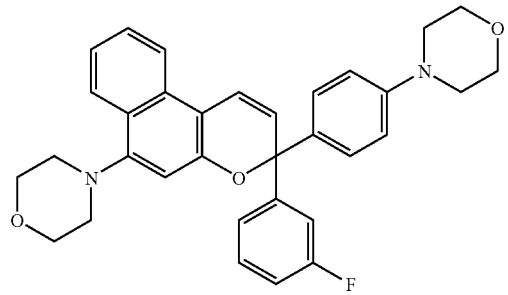

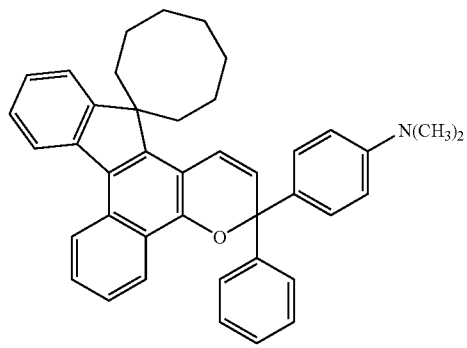

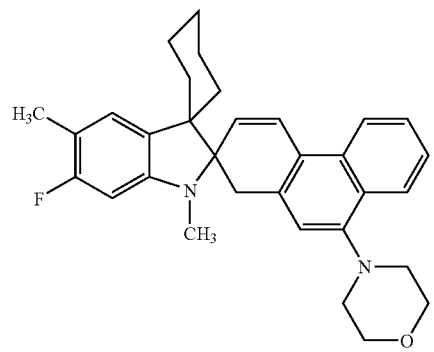

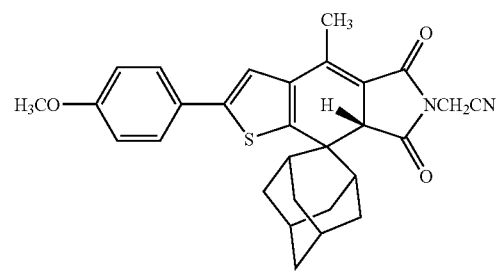

EXAMPLES

The invention will be described in further detail by way of Examples to which only, however, the invention is in no way limited.

Example 1

A naphthol derivative and a propargyl alcohol derivative expressed by the following formulas were used.

Naphthol Derivative:

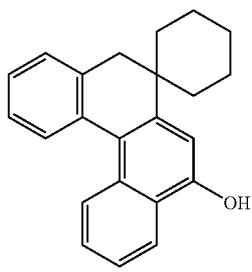

Propargyl Alcohol Derivative:

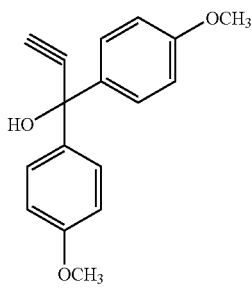

6.3 Grams (20 mmols) of the naphthol derivative and 5.9 g (22 mmols) of the propargyl alcohol derivative were dissolved in 300 ml of toluene to which was further added 0.05 g of a p-toluenesulfonic acid, and the mixture was stirred for 30 minutes while being heated and refluxed. After the reaction, the solvent was removed and the reaction product was refined by chromatography on silica gel to obtain 3.5 g of a white powdery product.

The product presumed to be $C_{40}H_{36}O_3$ was elementally analyzed and calculated to be as follows:

Elemental analysis: C, 85.23%, H, 6.38%, O: 8.39%
Calculated: C, 85.08%, H, 6.42%, O: 8.50%

Measurement of proton nuclear magnetic resonance spectra indicated a peak of 18H near δ 1.0 to 4.0 ppm based on alkylene group and a peak of 18H near near δ 5.2 to 10.0 ppm based on an aromatic proton and a proton of an alkene.

Further, measurement of $^{13}C$-nuclear magnetic resonance spectra indicated a peak near δ 110 to 160 ppm based on a carbon atom of an aromatic ring, a peak near δ 80 to 140 ppm based on a carbon atom of an alkene, and a peak at δ 20 to 60 ppm based on a carbon atom of an alkyl.

From the above results, it was confirmed that the isolated product was a compound represented by the following structural formula.

Structural Formula of the Isolated Product:

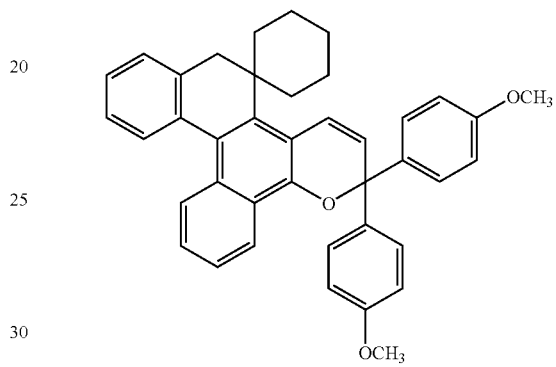

Examples 2 to 24

Chromene compounds shown in Tables 1 to 6 were synthesized in the same manner as in Example 1 by using compounds shown in Tables 1 to 6 as naphthol derivatives and propargyl alcohol derivatives. The obtained products were confirmed for their structures relying on the same structure analysis as that of Example 1.

In the structural formulas shown in Tables 1 to 6, Me represents the methyl group.

TABLE 1

| Ex. No. | Compound No. | Staring material | | Product | Yield (%) |
|---|---|---|---|---|---|
| | | Naphthol derivative | Propagyl alcohol | | |
| 2 | 2 | | | | 25 |

TABLE 1-continued

| Ex. No. | Compound No. | Starting material | | Product | Yield (%) |
|---|---|---|---|---|---|
| | | Naphthol derivative | Propagyl alcohol | | |
| 3 | 3 | [structure] | [structure] | [structure] | 30 |
| 4 | 4 | [structure] | [structure] | [structure] | 21 |
| 5 | 5 | [structure] | [structure] | [structure] | 18 |

TABLE 2

| Ex. No. | Compound No. | Starting material | | Product | Yield (%) |
|---|---|---|---|---|---|
| | | Naphthol derivative | Propargyl alcohol | | |
| 6 | 6 | (structure) | (structure) | (structure) | 22 |
| 7 | 7 | (structure) | (structure) | (structure) | 16 |
| 8 | 8 | (structure) | (structure) | (structure) | 18 |
| 9 | 9 | (structure) | (structure) | (structure) | 24 |

TABLE 3

| Ex. No. | Compound No. | Staring material | | Product | Yield (%) |
|---|---|---|---|---|---|
| | | Naphthol derivative | Propargyl alcohol | | |
| 10 | 10 | | | | 18 |
| 11 | 11 | | | | 17 |
| 12 | 12 | | | | 30 |
| 13 | 13 | | | | 28 |

TABLE 4

| Ex. No. | Compound No. | Staring material | | Product | Yield (%) |
|---|---|---|---|---|---|
| | | Naphthol derivative | Propargyl alcohol | | |
| 14 | 14 | | | | 16 |
| 15 | 15 | | | | 25 |
| 16 | 16 | | | | 21 |
| 17 | 17 | | | | 20 |

TABLE 5
| Ex. No. | Compound No. | Starting material | | Product | Yield (%) |
|---|---|---|---|---|---|
| | | Naphthol derivative | Propargyl alcohol | | |
| 18 | 18 | 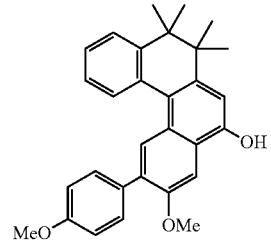 | 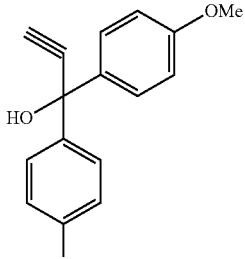 | 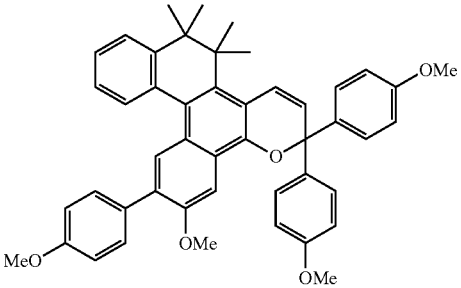 | 24 |
| 19 | 19 | 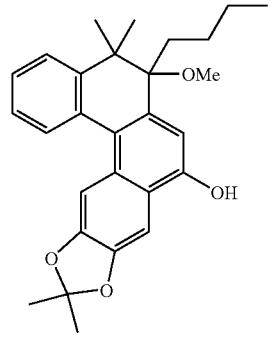 | 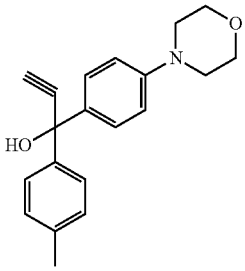 | 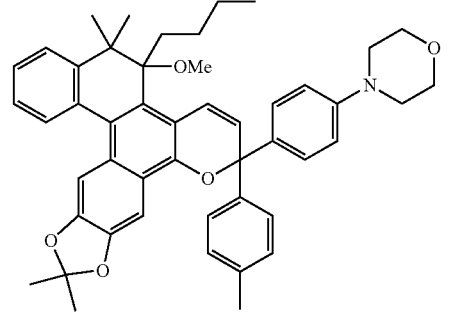 | 21 |
| 20 | 20 | 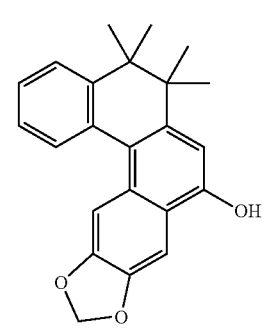 | 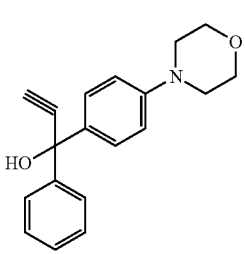 | 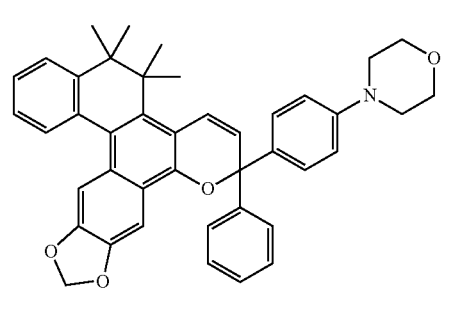 | 19 |
| 21 | 21 | 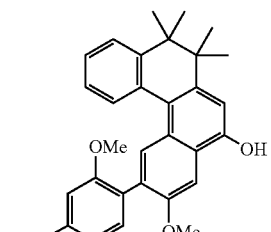 | 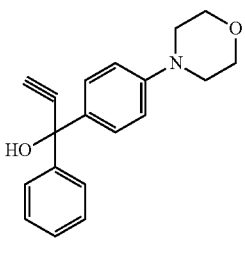 | 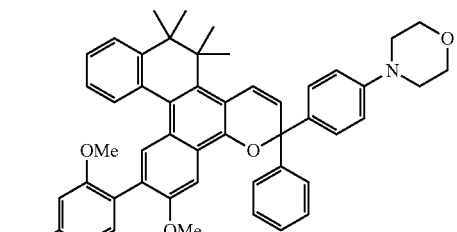 | 18 |

TABLE 6

| Ex. No. | Compound No. | Starting material | | Product | Yield (%) |
|---|---|---|---|---|---|
| | | Naphthol derivative | Propargyl alcohol | | |
| 22 | 22 | [structure] | [structure] | [structure] | 25 |
| 23 | 23 | [structure] | [structure] | [structure] | 16 |
| 24 | 24 | [structure] | [structure] | [structure] | 20 |

Example 25

A radically polymerizable monomer composition was prepared according to the following recipe.

Radically Polymerizable Monomer Composition:

| | |
|---|---|
| 2,2-Bis(4-methacryloyloxypentaethoxyphenyl)propane | 50 parts by mass |
| Polyethylene glycol diacrylate (average molecular weight, 532) | 10 parts by mass |
| Trimethylolpropane trimethacrylate | 10 parts by mass |
| Polyester oligomer hexaacrylate (EB-1830 manufactured by Dycel UCB Co.) | 10 parts by mass |
| Glycidyl methacrylate | 10 parts by mass |
| Chromene compound of Example 1 | 1 part by mass |

As the photopolymerization initiator, further, CGI1800 manufactured by Chiba Specialty Chemicals Co. was provided. This photopolymerization initiator is a mixture of 1-hydroxycyclohexylphenyl ketone and a bis(2,6-dimethoxybenzoyl)-2,4,4-trimethyl-pentylphosphinoxide (weight ratio of 3:1).

By using the above radically polymerizable monomer composition and the photopolymerization initiator, a photopolymerizable and curable composition was prepared by homogeneously mixing the components according to the following recipe.

Recipe of Photopolymerizable and Curable Composition:

| | |
|---|---|
| Radically polymerizable monomer composition | 91 parts by mass |
| Photopolymerization initiator | 0.5 parts by mass |
| Bis(1,2,2,6,6-pentamethyl-4-piperidyl)sebacate (stabilizer) | 5 parts by mass |

| | | |
|---|---|---|
| γ-Methacryloyloxypropyltrimethoxysilane (silane coupling agent) | 7 parts by mass | |
| N-methyldiethanolamine | 3 parts by mass | |

Next, about 2 g of the above photopolymerizable and curable composition was spin-coated onto the surface of the lens material (CR39 manufactured by Sunlux Co.: allyl resin plastic lens, refractive index=1.50) by using a spin coater, 1H-DX2, manufactured by Mikasa Co. The lens material of which the surface was coated was irradiated with light in a nitrogen gas atmosphere by using a metal halide lamp of an output of 120 mW/cm$^2$ for 3 minutes to cure the coating to thereby obtain a photochromic plastic lens.

To evaluate the cured state of the thin photochromic cured film (film thickness of 40 μm) of the obtained photochromic plastic lens, the surface of the film was rubbed with a cloth wetted with acetone, and the lens material was irradiated with light by using a projector to observe and evaluate the projected surface. If the curing is favorable, the surface is not invaded by acetone, and the surface exhibits no ruggedness or scratch. The basis of evaluation was as follows:

A: The surface is flat, has no ruggedness or scratch, and the thin film has been sufficiently cured.

B: The surface is locally and finely rugged and is scratched.

C: The surface is locally rugged and scratched.

D: The film is dissolving.

The photochromic plastic lenses produced according to the above-mentioned method were evaluated for their cured state to be A.

Further, the obtained photochromic plastic lenses were evaluated for their photochromic properties concerning the items (1) to (5) described below. The results were as shown in Table 7.

(1) Maximum Absorption Wavelength (λmax):

A maximum absorption wavelength after having developed color was found by using a spectrophotometer (instantaneous multi-channel photodetector MCPD3000) manufactured by Otsuka Denshi Kogyo Co. The maximum absorption wavelength is related to a color tone at the time of developing a color.

(2) Initial Coloring Degree [ε(0)]:

Absorbancy was measured at the maximum absorption wavelength in a state of not irradiated with light, and was regarded to be the initial coloring degree. In an optical material such as a spectacle lens, it can be said that the lower this value, the more the photochromic properties are excellent.

(3) Color Density [ε(120)−ε(0)]:

A difference was found between the absorbancy [ε(120)] at the maximum absorption wavelength after irradiated with light for 120 seconds and the above initial coloring degree [ε(0)], and was regarded to be the color density. It can be said that the higher this value, the more the photochromic properties are excellent.

(4) Fading Half-Life [$t_{1/2}$ (Min.)]:

A time was found until the absorbancy of the sample at the maximum wavelength decreased down to one-half the color density [ε(120)−ε(0)] when it was no longer irradiated with light after having been irradiated with light for 120 seconds, as a fading half-life. It can be said that the shorter this time, the larger the fading rate and the more excellent the photochromic properties.

(5) Degree of Deterioration [$(A_0-A_{200})$]:

To evaluate the resistance of color developed by the irradiation with light, the following deterioration acceleration testing was conducted. That is, the obtained polymer (sample) was aged for 200 hours in an accelerated manner by using a xenon weather meter, X25, manufactured by Suga Shikenki Co. Thereafter, the color density was evaluated before and after the testing. The color density ($A_0$) before the testing and the color density ($A_{200}$) after the testing were measured, and the degree of deterioration was found according to the following formula and was regarded to be an index of resistance of the developed color.

$$\text{Degree of deterioration} = (A_0-A_{200})/A_0$$

The lower the degree of deterioration, the higher the resistance of the developed color.

Examples 26 to 48

Photochromic plastic lenses were prepared in the same manner as in Example 25 but using the compounds obtained in Examples 2 to 25 as chromene compounds, and were evaluated for their properties. The results were as shown in Table 7.

TABLE 7

| Ex. No. | Compound No. | Amount of photopolymerization initiator (parts by wt.) | Cured state | λ max (nm) | Color density ε(120)−ε(0) | Fading half-life τ½ (min.) |
|---|---|---|---|---|---|---|
| 25 | 1 | 0.5 | A | 442 | 0.75 | 0.8 |
|  |  |  |  | 578 | 0.92 |  |
| 26 | 2 | 0.5 | A | 482 | 0.86 | 1.3 |
|  |  |  |  | 594 | 0.90 |  |
| 27 | 3 | 0.5 | A | 458 | 1.23 | 1.6 |
|  |  |  |  | 580 | 0.78 |  |
| 28 | 4 | 0.5 | A | 440 | 0.80 | 1.2 |
|  |  |  |  | 582 | 0.85 |  |
| 29 | 5 | 0.5 | A | 444 | 0.73 | 1.1 |
|  |  |  |  | 588 | 0.81 |  |
| 30 | 6 | 0.5 | A | 462 | 0.84 | 1.4 |
|  |  |  |  | 590 | 1.02 |  |
| 31 | 7 | 0.5 | A | 446 | 0.81 | 1.3 |
|  |  |  |  | 586 | 0.92 |  |
| 32 | 8 | 0.5 | A | 446 | 0.78 | 1.4 |
|  |  |  |  | 588 | 0.89 |  |
| 33 | 9 | 0.5 | A | 464 | 0.84 | 1.4 |
|  |  |  |  | 594 | 0.58 |  |
| 34 | 10 | 0.5 | A | 458 | 0.94 | 1.2 |
|  |  |  |  | 582 | 0.60 |  |

TABLE 7-continued

| Ex. No. | Compound No. | Amount of photo-polymerization initiator (parts by wt.) | Cured state | λ max (nm) | Color density $\epsilon(120)$-$\epsilon(0)$ | Fading half-life $\tau^{1/2}$ (min.) |
|---|---|---|---|---|---|---|
| 35 | 11 | 0.5 | A | 440 | 1.15 | 1.5 |
|  |  |  |  | 576 | 0.68 |  |
| 36 | 12 | 0.5 | A | 470 | 0.76 | 1.5 |
|  |  |  |  | 590 | 0.93 |  |
| 37 | 13 | 0.5 | A | 450 | 0.98 | 1.7 |
|  |  |  |  | 588 | 0.83 |  |
| 38 | 14 | 0.5 | A | 486 | 1.33 | 2.0 |
|  |  |  |  | 608 | 0.83 |  |
| 39 | 15 | 0.5 | A | 444 | 0.92 | 1.4 |
|  |  |  |  | 586 | 1.04 |  |
| 40 | 16 | 0.5 | A | 462 | 1.03 | 1.1 |
|  |  |  |  | 590 | 0.77 |  |
| 41 | 17 | 0.5 | A | 472 | 0.71 | 1.5 |
|  |  |  |  | 594 | 0.86 |  |
| 42 | 18 | 0.5 | A | 454 | 0.82 | 1.5 |
|  |  |  |  | 588 | 0.81 |  |
| 43 | 19 | 0.5 | A | 468 | 0.72 | 1.1 |
|  |  |  |  | 592 | 0.83 |  |
| 44 | 20 | 0.5 | A | 466 | 0.79 | 1.3 |
|  |  |  |  | 588 | 0.87 |  |
| 45 | 21 | 0.5 | A | 472 | 0.73 | 1.7 |
|  |  |  |  | 594 | 0.84 |  |
| 46 | 22 | 0.5 | A | 458 | 1.09 | 1.2 |
|  |  |  |  | 584 | 0.81 |  |
| 47 | 23 | 0.5 | A | 438 | 0.78 | 0.9 |
|  |  |  |  | 566 | 0.96 |  |
| 48 | 24 | 0.5 | A | 470 | 0.80 | 1.3 |
|  |  |  |  | 592 | 0.89 |  |

Comparative Examples 1 to 4

For comparison, a compound A represented by the following formula (A) and a compound B represented by the following formula (B) were provided.
Compound A:

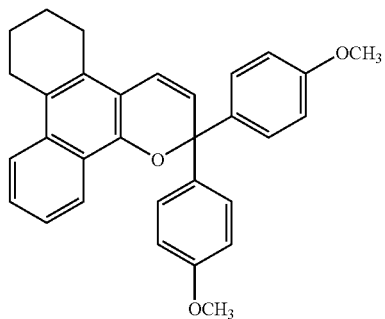

(A)

Compound B:

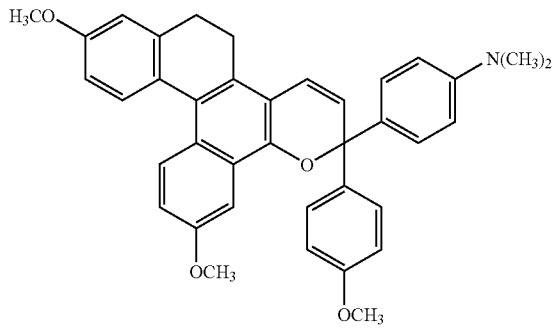

(B)

It was attempted to produce photochromic plastic lenses (Comparative Examples 1 and 2) in the same manner as in Example 25 but using the above compound A or the compound B instead of the chromene compound of Example 1. However, the films were not cured and could not be evaluated like in Example 25.

As shown in Table 8, further, photochromic plastic lenses were produced in the same manner as in Comparative Example 1 or Comparative Example 2 but using the photopolymerization initiator in an increased amount (Comparative Examples 3 and 4). In the case of Comparative Example 3 using the compound A, the film was not cured like in Comparative Examples 1 and 2, and could not be evaluated. In the case of Comparative Example 4 using the compound B, on the other hand, the film was partly cured but its photochromic properties were poor. The results of evaluation were as shown in Table 8.

TABLE 8

| Comp. Ex. No. | Compound No. | Amount of photo-polymerization initiator (parts by wt.) | Cured state | λ max (nm) | color density ϵ(120)-ϵ(0) | Fading half-life τ½ (min.) |
|---|---|---|---|---|---|---|
| 1 | A | 0.5 | D (not cured) | | could not be measured | |
| 2 | B | 0.5 | D (not cured) | | could not be measured | |
| 3 | A | 2 | D (not cured) | | could not be measured | |
| 4 | B | 2 | C | 496 | 0.05 | could not be measured |
| | | | | 590 | 0.06 | |

Example 49

Next, a photochromic cured body obtained by the in-mass method was evaluated as described below.

First, a thermoradically polymerizable composition was prepared according to the following recipe.

Recipe of the Thermoradically Polymerizable Composition:

| | |
|---|---|
| Chromene compound of Example 1 | 0.04 parts by mass |
| Tetraethylene glycol dimethacrylate | 13 parts by mass |
| 2,2-Bis[4-(methacryloxyethoxy)phenyl]propane | 48 parts by mass |
| Polyethylene glycol monoallyl ether | 2 parts by mass |
| Trimethylolpropane trimethacrylate | 20 parts by mass |
| Glycidyl methacrylate | 9 parts by mass |
| t-Butylperoxy 2-ethyl hexanoate (polymerization initiator) | 1 part by mass |

The thermoradically polymerizable composition obtained above was poured into a mold constituted by glass plates and a gasket of an ethylene/vinyl acetate copolymer, and was cast-polymerized. The cast polymerization was conducted by holding the mold in an air furnace while gradually elevating the temperature from 30° C. up to 90° C. over 18 hours, and the mold was maintained at a temperature of 90° C. for 2 hours. After the polymerization, the cured body was taken out from the glass mold in the mold. The obtained cured body (2 mm thick) was used as a sample and was evaluated for its photochromic properties by the same method as the one described above. The results were as shown in Table 9.

Examples 50 to 72

Photochromic cured bodies were obtained by the cast polymerization in the same manner as in Example 49 but using the chromene compounds obtained in Examples 2 to 24, and were evaluated for their properties. The results were as shown in Table 9.

TABLE 9

| Ex. No. | Compound No. | λ max (nm) | Color density ϵ(120)-ϵ(0) | Fading half-life τ½ (min.) | Degree of deterioration (A0 − A200)/A0 × 100 |
|---|---|---|---|---|---|
| 49 | 1 | 442 | 0.69 | 1.2 | 14% |
| | | 578 | 0.85 | | |
| 50 | 2 | 482 | 0.79 | 1.5 | 14% |
| | | 594 | 0.83 | | |
| 51 | 3 | 458 | 1.15 | 1.8 | 16% |
| | | 580 | 0.72 | | |
| 52 | 4 | 440 | 076 | 1.5 | 19% |
| | | 582 | 0.80 | | |
| 53 | 5 | 444 | 0.69 | 1.4 | 18% |
| | | 588 | 0.77 | | |
| 54 | 6 | 462 | 0.80 | 1.7 | 15% |
| | | 590 | 0.98 | | |
| 55 | 7 | 446 | 0.76 | 1.6 | 17% |
| | | 586 | 0.87 | | |
| 56 | 8 | 446 | 0.73 | 1.8 | 17% |
| | | 588 | 0.83 | | |
| 57 | 9 | 464 | 0.76 | 1.9 | 15% |
| | | 594 | 0.52 | | |
| 58 | 10 | 458 | 0.85 | 1.4 | 14% |
| | | 582 | 0.54 | | |
| 59 | 11 | 440 | 1.04 | 1.7 | 19% |
| | | 576 | 0.61 | | |
| 60 | 12 | 470 | 0.71 | 1.8 | 13% |
| | | 590 | 0.87 | | |
| 61 | 13 | 450 | 0.92 | 2.1 | 16% |
| | | 588 | 0.78 | | |
| 62 | 14 | 486 | 1.22 | 2.3 | 13% |
| | | 608 | 0.76 | | |
| 63 | 15 | 444 | 0.85 | 1.6 | 15% |
| | | 586 | 0.96 | | |
| 64 | 16 | 462 | 0.97 | 1.3 | 14% |
| | | 590 | 0.72 | | |
| 65 | 17 | 472 | 0.66 | 1.8 | 15% |
| | | 594 | 0.80 | | |
| 66 | 18 | 454 | 0.74 | 1.9 | 14% |
| | | 588 | 0.73 | | |
| 67 | 19 | 468 | 0.65 | 1.3 | 17% |
| | | 592 | 0.75 | | |
| 68 | 20 | 466 | 0.71 | 1.6 | 14% |
| | | 588 | 0.78 | | |
| 69 | 21 | 472 | 0.69 | 2.0 | 14% |
| | | 594 | 0.79 | | |
| 70 | 22 | 458 | 1.02 | 1.5 | 15% |
| | | 584 | 0.76 | | |
| 71 | 23 | 438 | 0.72 | 1.1 | 20% |
| | | 566 | 0.88 | | |
| 72 | 24 | 470 | 0.74 | 1.6 | 18% |
| | | 592 | 0.82 | | |

Comparative Examples 5 and 6

For comparison, photochromic cured bodies were obtained by the cast polymerization in the same manner as in Example 49 but using the above compound A or the compound B instead of using the chromene compound of Example 1, and were evaluated for their properties. The results were as shown in Table 10.

TABLE 10

| Comp. Ex. No. | Compound No. | λ max (nm) | Color density ϵ(120)-ϵ(0) | Fading half-life τ½ (min.) | Degree of deterioration (A0 − A200)/A0 × 100 |
|---|---|---|---|---|---|
| 5 | A | 522 | 0.79 | 8.3 | 32% |
| 6 | B | 498 | 0.85 | 4.1 | 29% |
| | | 596 | 0.78 | | |

The cured bodies obtained by the in-mass method of Examples 49 to 72 have higher recurring resistances in the photochromic properties than those of the cured bodies obtained in Comparative Examples 5 and 6. Further, the cured bodies obtained in Examples 49 to 72 have shorter fading half-lives (higher fading rates) than those of the cured bodies obtained in Comparative Examples 5 and 6, and are superior in this regard, too.

The invention claimed is:

1. A photochromic curable composition comprising
a polymerizable monomer;
a chromene compound represented by the following formula (1)

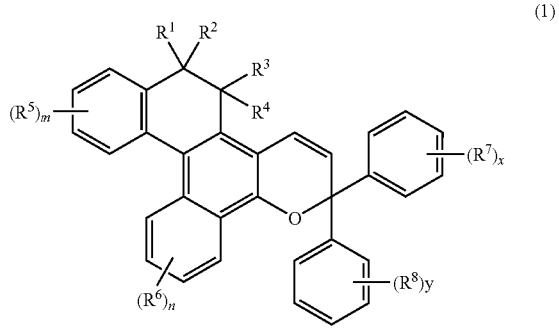

(1)

wherein $R^1$ and $R^2$ are independently hydrogen atoms, hydroxyl groups, alkyl groups, cycloalkyl groups, alkoxy groups, aralkyl groups, aralkoxy groups or aryl groups and optionally $R^1$ and $R^2$ are bonded together to form a ring or $R^3$ and $R^4$ are bonded together to form a ring, (a) $R^1$ and $R^3$ or $R^4$ are groups independent from each other, and $R^2$ and $R^3$ or $R^4$ are groups independent from each other; and (b) $R^3$ and $R^4$ are independently hydroxyl groups, alkyl groups, cycloalkyl groups, alkoxy groups, aralkyl groups, aralkoxy groups or aryl groups, $R^5$, $R^6$, $R^7$ and $R^8$ are independently, hydroxyl groups, alkyl groups, cycloalkyl groups, alkoxy groups, aralkyl groups, aralkoxy groups, aryl groups, amino groups, substituted amino groups, cyano groups, nitro groups, halogen atoms, halogenoalkyl groups or halogenoalkoxy groups, and when two $R^6$ are bonding to adjacent carbon atoms, bonded two group $R^6$ may form 1,3-dioxolan ring or 1,4-dioxane ring and these rings may have an alkyl group as a substituent, m and n are independently, integers of 0 to 4, and x and y are independently, integers of 0 to 5; and a photopolymerization initiator.

2. A photochromic optical article having, as a constituent member, a high molecular formed body in which the chromene compound of claim 1 is dispersed.

3. An optical article comprising an optical material and a high molecular film formed on at least one surface of the optical material, the high molecular film having a chromene compound of claim 1 dispersed therein.

4. The optical article according to claim 1, wherein said high molecular film is obtained by curing the photochromic curable composition of claim 1 by the photoradical polymerization.

* * * * *